(12) United States Patent
Choi et al.

(10) Patent No.: US 9,963,418 B2
(45) Date of Patent: May 8, 2018

(54) PURIFICATION METHOD OF PHOTOREACTIVE COMPOUND AND PHOTOREACTIVE COMPOUND

(71) Applicant: LG CHEM, LTD., Seoul (KR)

(72) Inventors: Dai Seung Choi, Daejeon (KR); Sung-Ho Chun, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days. days.

(21) Appl. No.: 14/909,426

(22) PCT Filed: Aug. 1, 2014

(86) PCT No.: PCT/KR2014/007139
§ 371 (c)(1),
(2) Date: Feb. 1, 2016

(87) PCT Pub. No.: WO2015/016680
PCT Pub. Date: Feb. 5, 2015

(65) Prior Publication Data
US 2016/0194269 A1 Jul. 7, 2016

(30) Foreign Application Priority Data

Aug. 2, 2013 (KR) .................. 10-2013-0091892
Jul. 31, 2014 (KR) .................. 10-2014-0098440

(51) Int. Cl.
*C07C 69/76* (2006.01)
*C07C 67/54* (2006.01)

(52) U.S. Cl.
CPC .......... *C07C 67/54* (2013.01); *C07C 2602/42* (2017.05)

(58) Field of Classification Search
CPC ..... C07C 67/54; C07C 69/65; C07C 2602/42; C07C 69/734; C07C 2102/42; C08F 120/40; C08G 61/00; C07B 63/00
See application file for complete search history.

(56) References Cited

U.S. PATENT DOCUMENTS

| | | | |
|---|---|---|---|
| 4,983,761 A | 1/1991 | Breuer et al. | |
| 5,464,669 A | 11/1995 | Kang et al. | |
| 7,198,878 B2 | 4/2007 | So et al. | |
| 2006/0160970 A1 | 7/2006 | Kim et al. | |
| 2010/0047481 A1* | 2/2010 | Choi | C07C 51/567 428/1.2 |
| 2010/0121005 A1* | 5/2010 | Kim | C08F 8/00 526/90 |
| 2011/0213048 A1 | 9/2011 | Yoo et al. | |

FOREIGN PATENT DOCUMENTS

| | | | |
|---|---|---|---|
| CN | 1497036 A | | 5/2004 |
| CN | 102216364 A | | 10/2011 |
| JP | 02157246 A | | 6/1990 |
| JP | 11-181127 A | | 7/1999 |
| JP | 2002-47318 A | | 2/2002 |
| JP | 2002-255902 A | | 9/2002 |
| JP | 2004-137467 A | | 5/2004 |
| JP | 2008-527103 A | | 7/2008 |
| JP | 2012515228 A | | 7/2012 |
| KR | 10-2006-0080552 A | | 7/2006 |
| KR | 10-2006-0084811 A | | 7/2006 |
| KR | 10-2008-0086408 A | | 9/2008 |
| KR | 10-2009-0047720 A | | 5/2009 |
| KR | 10-0960580 B1 | | 6/2010 |
| KR | 10-2010-0083103 A | | 7/2010 |
| KR | 10 2012 0007778 | * | 1/2012 |
| KR | 10-2012-0007778 A | | 1/2012 |

OTHER PUBLICATIONS

HLPD (High and low pressure distillation, published on the Web. 2000).*
M. Schadt, et al., "Surface-Induced Parallel Alignment of Liquid Crystals by Linearly Polymerized Photopolymers", Jpn. J. Appl. Phys., vol. 31., 1992, 2155.
Yuriy Reznikov, "Peculiarity of an Oblique Liquid Crystal Alignment Induced by a Photosensitive Orientant", Jpn. J. Appl. Phys. vol. 34, 1995, L1000.
Chemical Engineering Handbook, pp. 1314 to 1316, published on Apr. 10, 1972, Maruzen Co., Ltd.
Experimental Chemistry Book, pp. 124-126, Apr. 30, 1994, pp. 124-126, Apr. 30, 1994, Maruzen Co., Ltd.
Fenxi Ceshi Xuebao (Journal of Instrumental Analysis) vol. 22, No. 4, Jul. 2003.

* cited by examiner

*Primary Examiner* — Yevgeny Valenrod
*Assistant Examiner* — Blaine G Doletski
(74) *Attorney, Agent, or Firm* — Dentons US LLP

(57) ABSTRACT

Provided is a purification method of a photoreactive compound, and a photoreactive compound. According to the purification method of the present invention, a light and heat-sensitive photoreactive compound may be purified in high purity, thereby polymerizing a photoreactive polymer having improved physical properties.

8 Claims, No Drawings

PURIFICATION METHOD OF PHOTOREACTIVE COMPOUND AND PHOTOREACTIVE COMPOUND

BACKGROUND OF THE INVENTION (a) Field of the Invention

The present disclosure relates to a purification method of a photoreactive compound, and a photoreactive compound. More particularly, the present disclosure relates to a method of purifying a light and heat-sensitive photoreactive compound in high purity by molecular distillation.

This application is a National Stage Application of International Application No. PCT/KR2014/007139, filed on Aug. 1, 2014, which claims the benefit of Korean Patent Application No. 10-2013-0091892, filed on Aug. 2, 2013 and Korean Patent Application No. 10-2014-0098440, filed on Jul. 31, 2014, all of which are hereby incorporated by reference in their entirety for all purposes as if fully set forth herein.

(b) Description of the Related Art

In recent years, as a liquid crystal display has become bigger, its application has been expanded from personal mobile phone or notebook computer to home wall-mounted television, and thus it is required to ensure the high definition, the high quality, and the wide viewing angle in respects to the liquid crystal display. In particular, since a thin film transistor liquid crystal display (TFT-LCD) driven by a thin film transistor independently drives each of pixels, a response rate of the liquid crystal is very high, and thus a high-quality dynamic image can be realized. Accordingly, the application range thereof is expanded.

In order to use liquid crystals as an optical switch in the TFT-LCD, liquid crystals needs to be initially oriented in a predetermined direction on a thin film transistor, which is disposed in the most inner portion of a display cell. For this purpose, a liquid crystal alignment film is used.

To achieve the liquid crystal alignment in liquid crystal displays, a rubbing process of aligning liquid crystals by rubbing an alignment film, or a process of aligning liquid crystals by light (hereinafter, referred to as "photoalignment") has been used until now.

The photoalignment refers to a mechanism, in which a photosensitive group connected to a polymer generates a photoreaction due to linearly polarized UV, and in this procedure, a main chain of the polymer is unidirectionally aligned, thereby forming a photopolymerizable liquid crystal alignment film in which the liquid crystals are aligned.

A representative example thereof is a photoalignment by photopolymerization, which is announced by M. Schadt, et al. (Jpn. J. Appl. Phys., Vol31, 1992, 2155), Dae S. Kang, et al. (U.S. Pat. No. 5,464,669), and Yuriy Reznikov (Jpn. J. Appl. Phys. Vol. 34, 1995, L1000).

In these patent documents and papers, polycinnamate-based polymers such as PVCN (poly(vinyl cinnamate)) and PVMC (poly(vinyl methoxycinnamate)) are generally used as the photoalignment polymers. In the case of performing the photoalignment, the cycloaddition reaction [2+2] of the double bond [2+2] of cinnamate forms cyclobutane by UV, and thus an anisotropic property is formed to unidirectionally align liquid crystal molecules, leading to the alignment of the liquid crystals.

With regard to the known photoalignment polymers, Japanese Patent Laid-open Publication No. Hei11-181127 discloses a method of manufacturing a polymer-type alignment film including a main chain such as acrylate and methacrylate and a side chain containing a photosensitive group such as a cinnamate group, and an alignment film manufactured thereby. However, in this case, the polymer main chain has a poor thermal stability so that it has a negative impact on the stability of the alignment film. Also, it is not easy to control a photoreaction rate via cinnamate substituent groups.

To prepare the photoalignment polymer having excellent performances, a high-purity photoreactive compound is needed as a monomer. However, since the photoreactive compound is sensitive to light and heat and has a property of high boiling point, it is not easy to purify the photoreactive compound in high purity.

SUMMARY OF THE INVENTION

In order to solve the conventional problems, an object of the present invention is to provide a method of purifying a photoreactive compound in high purity, and a photoreactive compound.

To achieve the above object, an aspect of the present invention provides a method of purifying a photoreactive compound, the method including the steps of:

preparing a crude product including the photoreactive compound containing one or more photoreactive groups selected from the following Chemical Formulae 2 to 4 and a polymerizable unsaturated bond;

performing molecular distillation of the crude product including the photoreactive compound; and recovering the photoreactive compound.

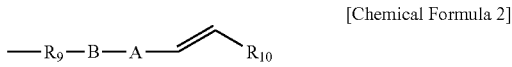
[Chemical Formula 2]

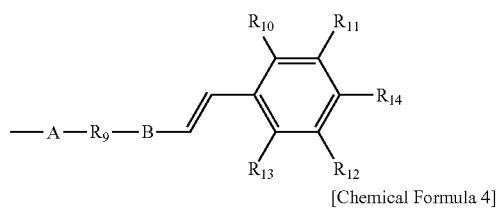
[Chemical Formula 3]

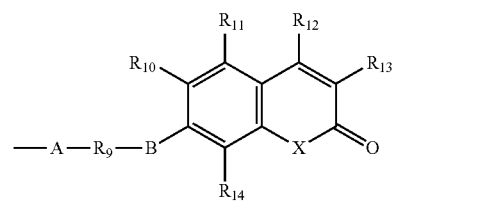
[Chemical Formula 4]

The substituents in Chemical Formulae 2, 3 and 4 will be described in detail below.

According to an embodiment, the step of performing molecular distillation of the crude product may be performed at a temperature of 50 to 300° C. and a pressure of 0.01 to 100 mmbar.

Further, according to an embodiment, the method may further include a step of performing preliminary distillation at a temperature of 20 to 200° C. and a pressure of 0.01 to 100 mmbar, prior to the step of performing molecular distillation of the crude product.

Further, another aspect of the present invention provides a photoreactive compound containing one or more photoreactive groups selected from Chemical Formulae 2 to 4 and a polymerizable unsaturated bond, and having an APHA value of less than 50.

According to the method of purifying the photoreactive compound of the present invention, the photoreactive compound may be purified in high purity, and the photoreactive compound thus purified may be used to obtain a photoalignment polymer having a high molecular weight in a high yield.

DETAILED DESCRIPTION OF THE EMBODIMENTS

A method of purifying a photoreactive compound of the present invention includes the steps of:

preparing a crude product including the photoreactive compound containing one or more photoreactive groups selected from the following Chemical Formulae 2 to 4 and a polymerizable unsaturated bond;

performing molecular distillation of the crude product including the photoreactive compound; and recovering the photoreactive compound.

[Chemical Formula 2]

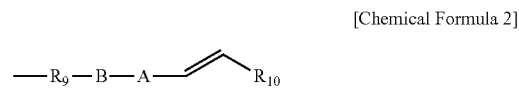

[Chemical Formula 3]

[Chemical Formula 4]

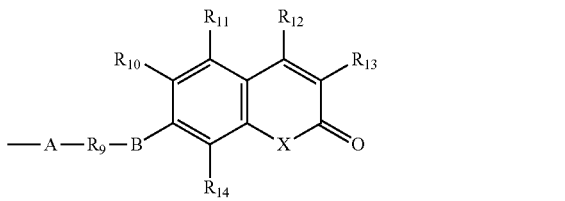

Further, the photoreactive compound of the present invention includes one or more photoreactive groups selected from Chemical Formulae 2 to 4 and a polymerizable unsaturated bond, and has an APHA value of less than 50.

The high-purity photoreactive compound obtained by the purification method of the present invention may be used to obtain a photoalignment polymer having a high molecular weight in a high yield.

Hereinafter, the present invention will be described in detail.

In a method of purifying a photoreactive compound of the present invention, a crude product including the photoreactive compound containing one or more photoreactive groups selected from the following Chemical Formulae 2 to 4 and a polymerizable unsaturated bond is prepared.

[Chemical Formula 2]

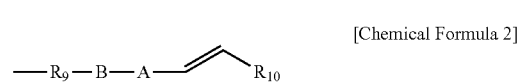

[Chemical Formula 3]

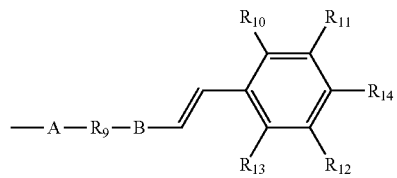

[Chemical Formula 4]

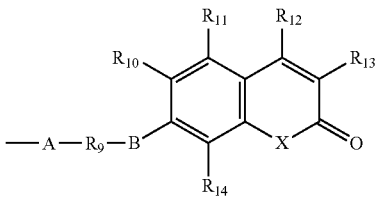

In Chemical Formula 2, 3 and 4, A is selected from a single bond, substituted or unsubstituted $C_1$-$C_{20}$ alkylene, carbonyl, carboxyl, substituted or unsubstituted $C_6$-$C_{40}$ arylene, and substituted or unsubstituted $C_6$-$C_{40}$ heteroarylene;

B is a single bond, oxygen, sulfur, or —NH—;

X is oxygen or sulfur;

$R_9$ is selected from a single bond, substituted or unsubstituted $C_1$-$C_{20}$ alkylene, substituted or unsubstituted $C_2$-$C_{20}$ alkenylene, substituted or unsubstituted $C_3$-$C_{12}$ cycloalkylene, substituted or unsubstituted $C_6$-$C_{40}$ arylene, substituted or unsubstituted $C_7$-$C_{15}$ aralkylene, and substituted or unsubstituted $C_2$-$C_{20}$ alkynylene; and $R_{10}$, $R_{11}$, $R_{12}$, $R_{13}$, and $R_{14}$ are the same as or different from each other, and each independently selected from the group consisting of hydrogen, a hydroxy group, a halogen group, substituted or unsubstituted $C_7$-$C_{15}$ aralkyl, substituted or unsubstituted $C_2$-$C_{20}$ alkynyl, substituted or unsubstituted $C_1$-$C_{20}$ alkyl, substituted or unsubstituted $C_1$-$C_{20}$ alkoxy, substituted or unsubstituted $C_6$-$C_{30}$ aryloxy, substituted or unsubstituted $C_6$-$C_{40}$ aryl, $C_6$-$C_{40}$ heteroaryl including a heteroatom of Group 14, Group 15, or Group 16, and substituted or unsubstituted $C_6$-$C_{40}$ alkoxyaryl.

According to an embodiment of the present invention, the photoreactive compound may be a vinyl-based compound, a cycloolefin-based compound having a double bond, or a (meth)acrylate-based compound.

Further, according to an embodiment of the present invention, the photoreactive compound may be represented by the following Chemical Formula 1:

[Chemical Formula 1]

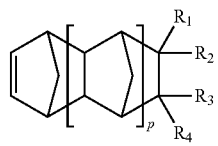

wherein p is an integer of 0 to 4, at least one of $R_1$, $R_2$, $R_3$, and $R_4$ is a radical selected from the group consisting of the following Chemical Formulae 2, 3 and 4, the others are each independently hydrogen, halogen, substituted or unsubstituted $C_1$-$C_{20}$ alkyl, substituted or unsubstituted $C_2$-$C_{20}$ alkenyl, substituted or unsubstituted $C_3$-$C_{12}$ cycloalkyl, substituted or unsubstituted $C_6$-$C_{40}$ aryl, substituted or unsubstituted $C_7$-$C_{15}$ aralkyl; substituted or unsubstituted $C_2$-$C_{20}$ alkynyl, or a polar functional group including a non-hydrocarbonaceous polar group containing at least one element selected from the group consisting of oxygen, nitrogen, phosphorus, sulfur, silicon, and boron, and if $R_1$, $R_2$, $R_3$, and $R_4$ are not hydrogen, halogen, or a polar functional group, $R_1$ and $R_2$, or $R_3$ and $R_4$ may be connected to each other to form a $C_1$-$C_{10}$ alkylidene group, or $R_1$ or $R_2$ may be connected to any one of $R_3$ and $R_4$ to form a $C_4$-$C_{12}$ saturated or unsaturated cyclic group or a $C_6$-$C_{24}$ aromatic ring compound;

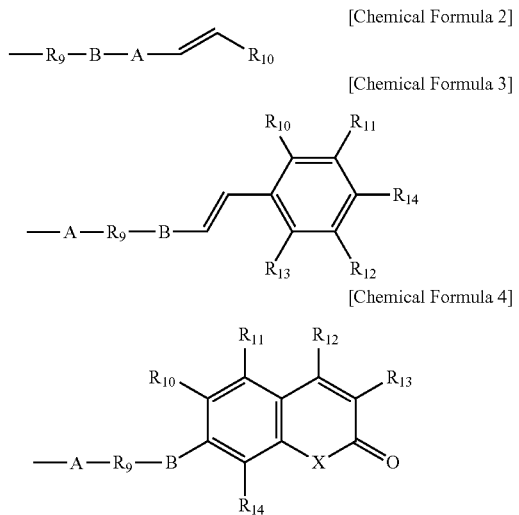

[Chemical Formula 2]

[Chemical Formula 3]

[Chemical Formula 4]

The substituents in Chemical Formulae 2, 3 and 4 are the same as defined above.

According to an embodiment of the present invention, $R_1$ of Chemical Formula 1 may be a compound represented by Chemical Formula 2, and at least one of $R_2$, $R_3$, and $R_4$ may be selected from the group consisting of Chemical Formulae 2, 3 and 4.

In this regard, the non-hydrocarbonaceous polar group may include the following compounds:

one or more selected from the group consisting of —$OR_6$, —$R_5OR_6$, —$OC(O)OR_6$, —$R_5OC(O)OR_6$, —$C(O)OR_6$, —$R_5C(O)OR_6$, —$C(O)R_6$, —$R_5C(O)R_6$, —$OC(O)R_6$, —$R_5OC(O)R_6$, —$(R_5O)_p$—$OR_6$ (p is an integer of 1 to 10), —$(OR_5)_p$—$OR_6$ (p is an integer of 1 to 10), —$C(O)$—$O$—$C(O)R_6$, —$R_5C(O)$—$O$—$C(O)R_6$, —$SR_6$, —$R_5SR_6$, —$SSR_6$, —$R_5SSR_6$, —$S(=O)R_6$, —$R_5S(=O)R_6$, —$R_5C(=S)R_6$, —$R_5C(=S)SR_6$, —$R_5SO_3R_6$, —$SO_3R_6$, —$R_5N=C=S$, —$N=C=S$, —$NCO$, $R_5$—$NCO$, —$CN$, —$R_5CN$, —$NNC(=S)R_6$, —$R_5NNC(=S)R_6$, —$NO_2$, —$R_5NO_2$,

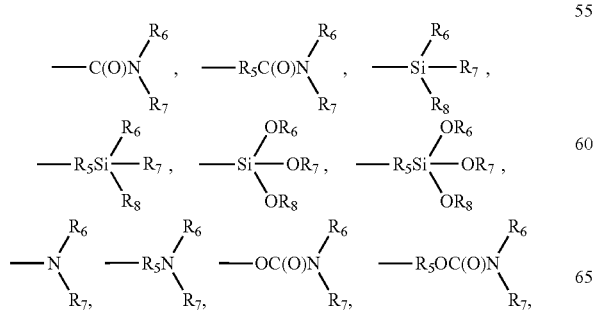

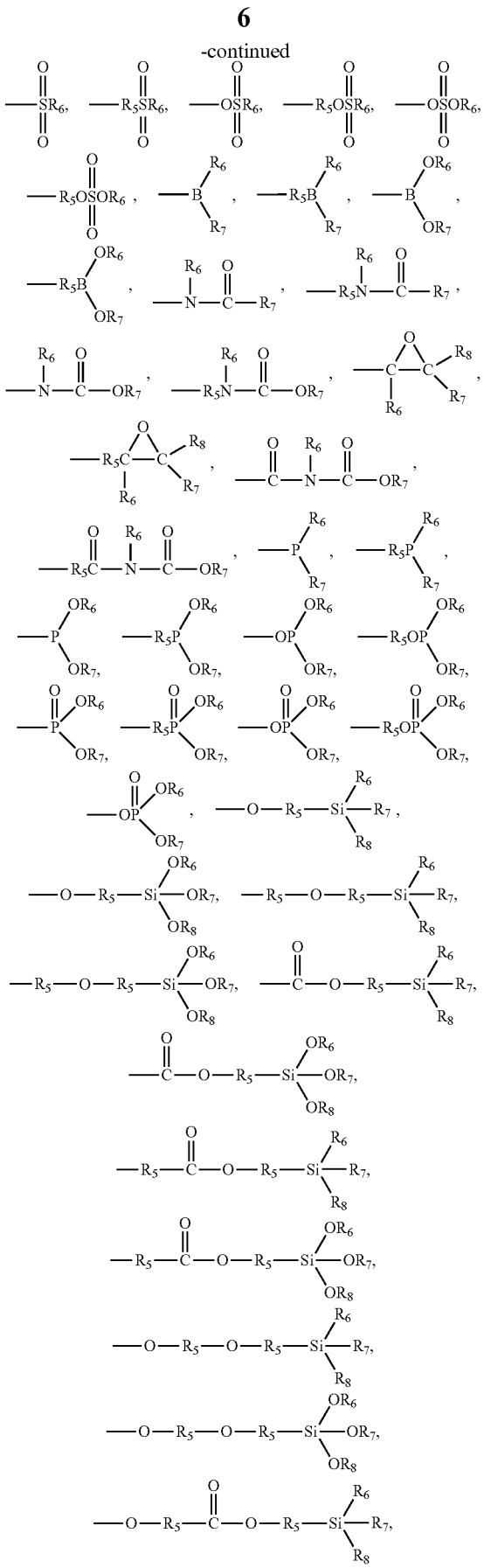

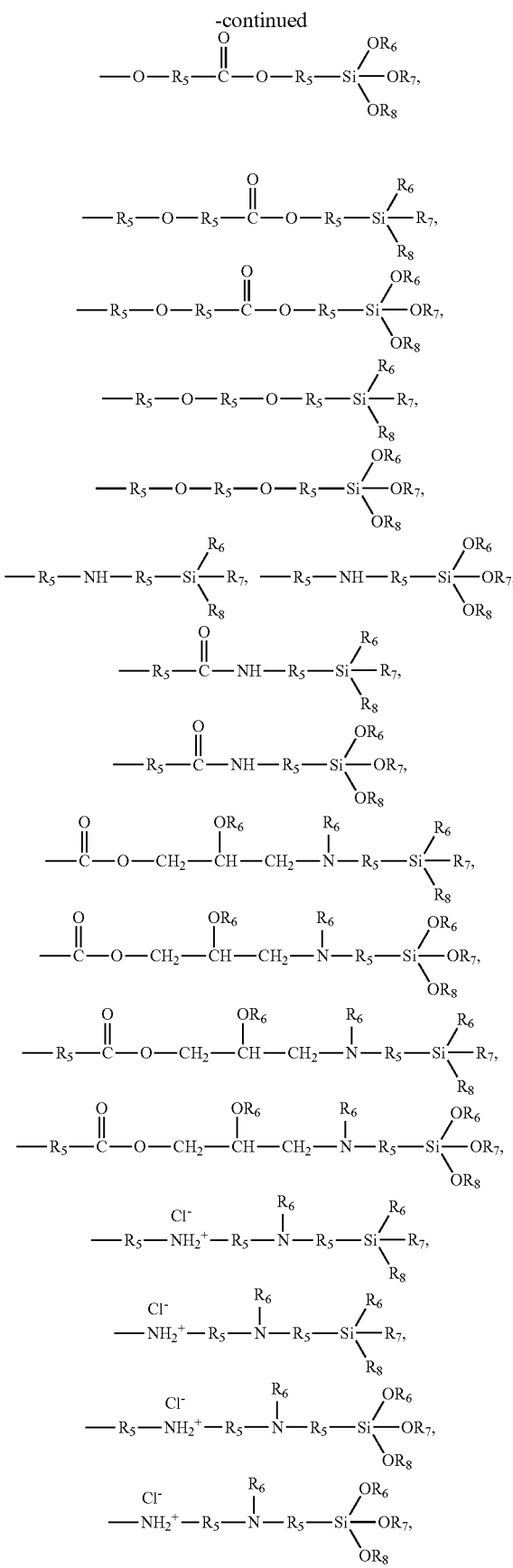

in the functional groups, each $R_5$ may be selected from substituted or unsubstituted $C_1$-$C_{20}$ alkylene, substituted or unsubstituted $C_2$-$C_{20}$ alkenylene, substituted or unsubstituted $C_3$-$C_{12}$ cycloalkylene, substituted or unsubstituted $C_6$-$C_{40}$ arylene, substituted or unsubstituted $C_7$-$C_{15}$ aralkylene, and substituted or unsubstituted $C_2$-$C_{20}$ alkynylene, and $R_6$, $R_7$, and $R_8$ may be each independently selected from hydrogen, halogen, substituted or unsubstituted $C_1$-$C_{20}$ alkyl, substituted or unsubstituted $C_2$-$C_{20}$ alkenyl, substituted or unsubstituted $C_3$-$C_{12}$ cycloalkyl, substituted or unsubstituted $C_6$-$C_{40}$ aryl, substituted or unsubstituted $C_7$-$C_{15}$ aralkyl, and substituted or unsubstituted $C_2$-$C_{20}$ alkynyl.

Further, according to an embodiment of the present invention, $C_6$-$C_{40}$ aryl and $C_6$-$C_{40}$ heteroaryl containing a heteroatom of Group 14, 15, or 16 in the substituents may include the following Chemical Formulae:

-continued

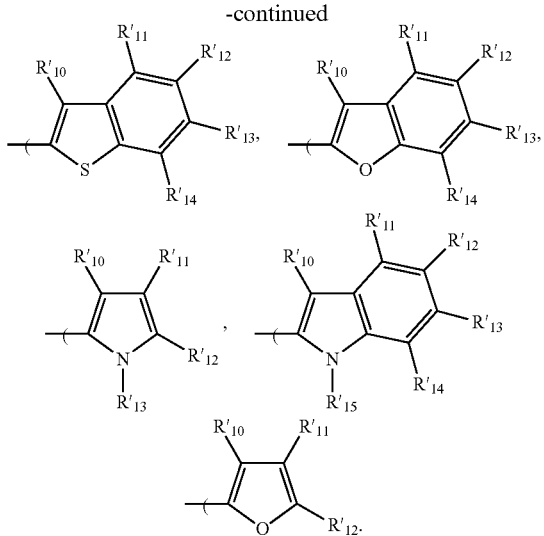

wherein at least one of R'$_{10}$ to R'$_{18}$ should be substituted or unsubstituted C$_1$-C$_{20}$ alkoxy, or substituted or unsubstituted C$_6$-C$_{30}$ aryloxy, and the others may be each independently selected from the group consisting of substituted or unsubstituted C$_1$-C$_{20}$ alkyl, substituted or unsubstituted C$_1$-C$_{20}$ alkoxy, substituted or unsubstituted C$_6$-C$_{30}$ aryloxy, and substituted or unsubstituted C$_6$-C$_{40}$ aryl.

Meanwhile, the detailed definition of the above described substituents is as follows:

The term "alkyl" refers to a straight or branched, saturated monovalent hydrocarbon with 1 to 20 carbon atoms, preferably 1 to 10 carbon atoms, and more preferably 1 to 6 carbon atoms. The alkyl group may be substituted with one or more halogen substituents, etc. Examples of the alkyl group include methyl, ethyl, propyl, 2-propyl, n-butyl, iso-butyl, tert-butyl, pentyl, hexyl, dodecyl, fluoromethyl, difluoromethyl, trifluoromethyl, chloromethyl, dichloromethyl, trichloromethyl, iodomethyl, bromomethyl or the like.

The term "alkenyl" refers to a linear or branched, monovalent hydrocarbon of 2 to 20 carbon atoms, preferably 2 to 10 carbon atoms, and more preferably 2 to 6 carbon atoms, which includes one or more carbon-carbon double bonds. The alkenyl group may be bound through a carbon atom including a carbon-carbon double bond or a saturated carbon atom. The alkenyl group may be substituted with one or more halogen substituents, etc. Examples of the alkenyl group include ethenyl, 1-prophenyl, 2-prophenyl, 2-butenyl, 3-butenyl, pentenyl, 5-hexenyl, dodecenyl or the like.

The term "cycloalkyl" refers to a saturated or unsaturated non-aromatic monovalent monocyclic, bicyclic, or tricyclic hydrocarbon of 3 to 12 cyclic carbon atoms, and may be substituted with one or more halogen substituents, etc. Examples of the cycloalkyl group include cyclopropyl, cyclobutyl, cyclopentyl, cyclopentenyl, cyclohexyl, cyclohexenyl, cycloheptyl, cyclooctyl, decahydronaphtalenyl, adamantyl, norbornyl (e.g., bicyclo [2,2,1] hept-5-enyl) or the like.

The term "aryl" refers to a monovalent monocyclic, bicyclic, or tricyclic aromatic hydrocarbon having 6 to 20, preferably 6 to 12 cyclic atoms, and may be substituted with one or more halogen substituents. Examples of the aryl group may include phenyl, naphthalenyl, fluorenyl or the like.

The term "alkoxyaryl" refers to an aryl radical in which one or more hydrogen atoms of the aryl group defined as described above are substituted with the alkoxy group. Examples of the alkoxyaryl group may include methoxyphenyl, ethoxyphenyl, propoxyphenyl, butoxyphenyl, pentoxyphenyl, heptoxyphenyl, heptoxy, octoxy, nanoxy, methoxybiphenyl, methoxynaphthalenyl, methoxyfluorenyl, methoxyanthracenyl or the like.

The term "aralkyl" refers to an akyl radical in which one or more hydrogen atoms of the alkyl group defined as described above are substituted with the aryl group, and may be substituted with one or more halogen substituents. Examples of the aralkyl may include benzyl, benzhydril, tritile or the like.

The term "alkynyl" refers to a linear or branched, monovalent hydrocarbon of 2 to 20 carbon atoms, preferably 2 to 10 carbon atoms, and more preferably 2 to 6 carbon atoms, which includes one or more carbon-carbon triple bonds. The alkynyl group may be bound through a carbon atom including a carbon-carbon triple bond or a saturated carbon atom. The alkynyl group may be substituted with one or more halogen substituents. Examples of the alkynyl group may include ethynyl, propynyl or the like.

The term "alkylene" refers to a linear or branched, saturated divalent hydrocarbon of 1 to 20 carbon atoms, preferably 1 to 10 carbon atoms, and more preferably 1 to 6 carbon atoms. The alkylene group may be substituted with one or more halogen substituents. Examples of the alkylene group may include methylene, ethylene, propylene, butylene, hexylene or the like.

The term "alkenylene" refers to a linear or branched, divalent hydrocarbon of 2 to 20 carbon atoms, preferably 2 to 10 carbon atoms, and more preferably 2 to 6 carbon atoms, which includes one or more carbon-carbon double bonds. The alkenylene group may be bound through a carbon atom including a carbon-carbon double bond and/or a saturated carbon atom. The alkenylene group may be substituted with one or more halogen substituents.

The term "cycloalkylene" refers to a saturated or unsaturated non-aromatic divalent monocyclic, bicyclic or tricyclic hydrocarbon having 3 to 12 cyclic carbons, and may be substituted with one or more halogen substituents. Examples of the cycloalkylene may include cyclopropylene, cyclobutylene or the like.

The term "arylene" refers to an aromatic divalent monocyclic, bicyclic or tricyclic hydrocarbon having 6 to 20 cyclic atoms, preferably 6 to 12 cyclic atoms, and may be substituted with one or more halogen substituents. The aromatic portion of the arylene group includes carbon atoms only. Examples of the arylene group include phenylene or the like.

The term "aralkylene" refers to a divalent portion in which one or more hydrogen atoms of the alkyl group defined as described above are substituted with the aryl group, and may be substituted with one or more halogen substituents. Examples of the aralkylene group may include benzylene or the like.

The term "alkynylene" refers to a linear or branched, divalent hydrocarbon of 2 to 20 carbon atoms, preferably 2 to 10 carbon atoms, and more preferably 2 to 6 carbon atoms, which includes one or more carbon-carbon triple bonds. The alkynylene group may be bound through a carbon atom including a carbon-carbon triple bond or a saturated carbon atom. The alkynylene group may be substituted with one or more halogen substituents. Examples of the alkynylene group may include ethynylene, propynylene and the like.

According to an embodiment of the present invention, the photoreactive compound represented by Chemical Formula 1 may be synthesized by, for example, a method disclosed in Korean Patent Publication No. 2009-0047720.

The crude product obtained by the method includes volatile compounds including a solvent and a starting material, or impurities such as oligomers, as well as the photoreactive compound.

In the purification method of the photoreactive compound according to the present invention, the crude product including the photoreactive compound is subjected to molecular distillation.

There is a high possibility that alkene, alkyne, alcohol, amine, thiol, phosphine compounds and other volatile compounds function to contaminate catalysts during polymerization reaction, thereby inhibiting polymerization activity. Further, these compounds may function as a chain transfer during polymerization reaction to produce a polymer having a lower molecular weight than a desired molecular weight. To prevent these problems, there is a need to remove various volatile compounds.

Further, oligomers remain in final polymers to inhibit thermal stability, and also inhibit optical and mechanical properties of the polymers. In some cases, oligomers per se inhibit polymerization activity, finally leading to yield reduction.

Therefore, it is necessary to remove volatile compounds and oligomers via the distillation process of the crude product as much as possible.

Meanwhile, the photoreactive compound, which is a purification object of the purification method of the present invention, has a characteristic of having a high boiling point, and therefore, it is difficult to distill the photoreactive compound by a general distillation method. For example, the above described photoreactive compound has a boiling point of about 180° C. or higher, for example, in the range from about 180 to about 300° C., and therefore, it is not easy to purify the compound by a general vacuum distillation method.

The molecular distillation (short path distillation) is a distillation process performed under almost vacuum, and it can be performed at a relatively low temperature to separate only desired materials by distillation without collision with other materials. Further, paths between evaporation and condensation spaces are short, and therefore, it is possible to evaporate and concentrate a large amount of materials in a short time while minimizing destruction or damage of materials with low thermal stability. Further, since this process is performed at a much lower pressure than the general vacuum distillation, the process is suitable for distillation of the high-boiling point photoreactive compound which is a purification object of the present invention.

In the purification method of the present invention, a distillation apparatus used in the molecular distillation is available from MYERS-VACUUM, INCON, CHEMTECH SERVICE, ASAHI, ULVAC, VTA, or UIC, but is not always limited thereto.

According to an embodiment of the present invention, the molecular distillation process of the crude product including the photoreactive compound may be performed at a temperature of about 50 to about 300° C., preferably about 90 to about 240° C. If the distillation temperature is lower than 50° C., effective separation of impurities by distillation may not occur, and if the distillation temperature is higher than 300° C., the distillation object may be degraded due to heat.

According to an embodiment of the present invention, the molecular distillation process of the crude product including the photoreactive compound may be performed under vacuum or almost vacuum. For example, molecular distillation may be performed at a pressure of about 0.001 to about 100 mmbar, preferably about 0.001 to about 10 mmbar. If the pressure is lower than 0.001 mmbar, impurities that must be removed are also distilled to reduce purity. If the pressure is higher than 100 mmbar, vaporization of the compounds is not easy to decrease distillation efficiency.

Further, the distillation may be performed in a short time, for example, for about 5 to 400 seconds, preferably for about 20 to about 300 seconds.

According to an embodiment of the present invention, a preliminary distillation step may be further performed, prior to the distillation of the crude product.

The preliminary distillation is to remove a solvent which remains in the crude product during the preparation of the photoreactive compound, and it may be performed using an apparatus the same as or different from the distillation apparatus used in the molecular distillation. When the solvent remains in the crude product, the molecular weight of the polymer polymerized using the photoreactive compound is decreased to deteriorate physical properties of the polymer.

According to an embodiment of the present invention, the preliminary distillation may be performed at a temperature lower than the conditions of the molecular distillation, for example, at a temperature of about 20 to about 200° C. and at a pressure of about 0.01 to about 100 mmbar.

If the temperature of preliminary distillation is lower than 20° C., effective separation by distillation may not occur. If the temperature of preliminary distillation is higher than 200° C., impurities are also distilled to reduce purity.

If the pressure is lower than 0.001 mmbar, the solvent and low-boiling point impurities that must be removed are also distilled to reduce purity. If the pressure is higher than 100 mmbar, vaporization of the compounds may not easily occur to decrease distillation efficiency per time.

The photoreactive compound is recovered from the crude product which is subjected to molecular distillation after the preliminary distillation or without preliminary distillation.

The photoreactive compound recovered by the purification method of the present invention may have purity of about 90.0% or higher, preferably about 90.0 to about 99.9%, more preferably about 95.0 to about 99.9%.

The photoreactive compound which is obtained in high purity according to the purification method of the present invention may be used as a monomer to polymerize a photoreactive polymer.

The photoreactive polymer may be prepared by polymerizing the photoreactive compound obtained according to the purification method of the present invention in the presence of a catalytic mixture consisting of a precatalyst containing a Group 10 transition metal, a first cocatalyst for providing a Lewis base capable of being weakly coordinate bonded to the metal of the precatalyst, and optionally, a second cocatalyst for providing a compound containing a neutral Group 15 electron donor ligand. In this regard, the photoreactive polymer may be polymerized at a temperature of about 10 to about 200° C. If the reaction temperature is lower than 10° C., a polymerization activity becomes very low, and if the reaction temperature is higher than 200° C., degradation of the catalyst occurs.

Preferably, the catalytic mixture may include about 1 to about 1000 mol of the first cocatalyst for providing a Lewis base capable of being weakly coordinate bonded to the metal of the precatalyst, and optionally, about 1 to about 1000 mol of the second cocatalyst for providing a compound containing a neutral Group 15 electron donor ligand, based on 1 mol of the precatalyst containing a Group 10 transition metal. If the content of the first or second cocatalyst is lower than 1 mol, activation of the catalyst may not be properly achieved, and if the content is higher than 1000 mol, the catalytic activity may be reduced.

A compound having the Lewis base functional group, which easily participates in a Lewis acid-base reaction to be separated from a core metal, may be used as the precatalyst containing a Group 10 transition metal so that the Lewis base is easily separated by the first cocatalyst for providing a Lewis acid to convert the central transition metal into the catalytic active species. The compound may be exemplified by [(Allyl)Pd(Cl)]$_2$(Allylpalladium chloride dimer), (CH$_3$CO$_2$)$_2$Pd [Palladium(II)acetate], [CH$_3$COCH═C(O—)CH$_3$]$_2$Pd [Palladium(II) acetylacetonate], NiBr(NP(CH$_3$)$_3$)$_4$, [PdCl(NB)O(CH$_3$)]$_2$, etc.

Moreover, the first cocatalyst for providing the Lewis base capable of weakly coordinating with the metal of the precatalyst may include a compound, which easily reacts with the Lewis base to form vacancies in the transition metal and which weakly coordinates with the transition metal compound, in order to stabilize the transition metal or another compound for providing this. It is exemplified by Borane such as B(C$_6$F$_5$)$_3$, borate such as dimethylanilinium tetrakis(pentafluorophenyl)borate, alkyl aluminum such as methyl aluminoxane or Al(C$_2$H$_5$)$_3$, or transition metal halide such as AgSbF$_6$.

Further, the first cocatalyst and the second cocatalyst may be prepared into a salt, and used as a compound activating the catalyst. It is exemplified by a compound prepared by an ionic bond of alkyl phosphine and a borane compound.

The photoreactive compound obtained according to the purification method of the present invention may have a low APHA value of less than about 50, for example, less than about 0 to about 50, preferably less than about 0 to about 30, and more preferably less than about 0 to about 20 to exhibit an excellent color characteristic.

According to another aspect of the present invention, provided is a photoreactive compound containing one or more photoreactive groups selected from the following Chemical Formulae 2 to 4 and a polymerizable unsaturated bond, and having an APHA value of less than 50.

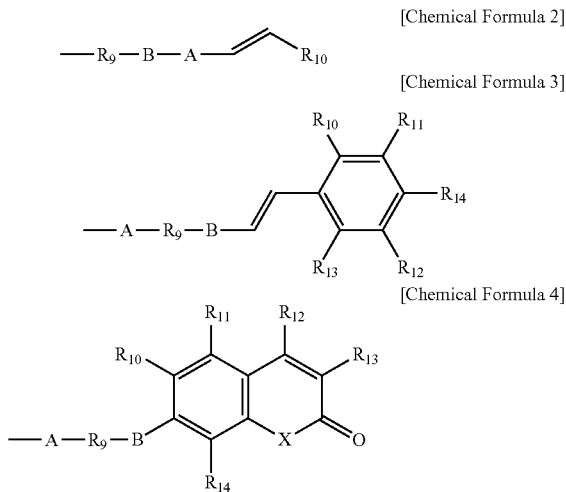

In Chemical Formulae 2, 3 and 4, A is selected from a single bond, substituted or unsubstituted C$_1$-C$_{20}$ alkylene, carbonyl, carboxyl, substituted or unsubstituted C$_6$-C$_{40}$ arylene and substituted or unsubstituted C$_6$-C$_{40}$ heteroarylene;

B is a single bond, oxygen, sulfur, or —NH—;

X is oxygen or sulfur;

R$_9$ is selected from a single bond, substituted or unsubstituted C$_1$-C$_{20}$ alkylene, substituted or unsubstituted C$_2$-C$_{20}$ alkenylene, substituted or unsubstituted C$_3$-C$_{12}$ cycloalkylene, substituted or unsubstituted C$_6$-C$_{40}$ arylene, substituted or unsubstituted C$_7$-C$_{15}$ aralkylene, and substituted or unsubstituted C$_2$-C$_{20}$ alkynylene; and R$_{10}$, R$_{11}$, R$_{12}$, R$_{13}$, and R$_{14}$ are the same as or different from each other, and each independently selected from the group consisting of hydrogen, a hydroxy group, a halogen group, substituted or unsubstituted C$_7$-C$_{15}$ aralkyl, substituted or unsubstituted C$_2$-C$_{20}$ alkynyl, substituted or unsubstituted C$_1$-C$_{20}$ alkyl, substituted or unsubstituted C$_1$-C$_{20}$ alkoxy, substituted or unsubstituted C$_6$-C$_{30}$ aryloxy, substituted or unsubstituted C$_6$-C$_{40}$ aryl, C$_6$-C$_{40}$ heteroaryl including a heteroatom of Group 14, Group 15, or Group 16, and substituted or unsubstituted C$_6$-C$_{40}$ alkoxyaryl.

The detailed description of the photoreactive compound and specific examples thereof may be the same as in the description of the purification method of the photoreactive compound.

The photoreactive compound may have a low APHA value of less than about 50, for example, less than about 0 to about 50, preferably less than about 0 to about 30, and more preferably less than about 0 to about 20 to exhibit an excellent color characteristic. The APHA value may be a value measured by dissolving the photoreactive compound in a MC(methyl chloride) solution in 10 wt % concentration.

The polymer polymerized using the photoreactive compound with high purity obtained according to the purification method of the present invention may have a high number average molecular weight and weight average molecular weight. For example, the polymer may have a number average molecular weight of about 10,000 to about 500,000 g/mol, and preferably about 20,000 to about 200,000 g/mol. Further, the polymer may have a weight average molecular weight of about 30,000 to about 1,000,000 g/mol, and preferably about 60,000 to about 300,000 g/mol.

Further, when the photoreactive compound with high purity obtained according to the purification method of the present invention is used, a photoreactive polymer may be polymerized in a high yield. According to an embodiment of the present invention, the photoreactive polymer may be polymerized in a yield of about 70 to about 90%, and preferably about 80 to about 98%.

The present invention will be described in more detail with reference to the following Examples. However, these Examples are for illustrative purposes only, and the invention is not intended to be limited by these Examples.

EXAMPLE

Example 1

Purification of 2-(4-propoxy cinnamic ester)-5-norbornene 5-norbornene-2-methanol (993.6 g, 8.0 mol), 4-propoxy cinnamic acid (1,650 g, 8.0 mol), and 2.0 L of xylene were injected to a 10 L-glass reactor. Zr(OAc)x(OH)y (38.8 g, 0.16 mol, 2 mol %) was injected thereto to perform azeotropic reflux under a mild nitrogen atmosphere. A temperature of a heating oil bath was adjusted to 190° C., and sampling of the solution was performed every time while reaction was allowed for about 1 day. The reaction was examined by GC.

26 hours later, termination of the reaction was confirmed by GC, and then the temperature was adjusted to 100° C., and the solvent xylene was removed under reduced pressure of 16 mbar. Thereafter, 4.0 L of ethyl acetate was added. After undissolved solid compounds subsided, washing was performed by addition of 2 L of 1.0 M (mol/L) dilute hydrochloric solution. This procedure was performed twice. Washing was performed by addition of 4 L of a saturated sodium hydrogen carbonate (NaHCO$_3$) aqueous solution. This procedure was also performed twice.

Magnesium sulfate (MgSO$_4$) was added to a separated organic solution to remove a small amount of water remaining in the solution. After removing water, magnesium sulfate was filtered and the solvent was removed under reduced pressure.

1,736 g of a liquid compound, 2-(4-propoxy cinnamic ester)-5-norbornene (hereinafter, referred to as NB-Cin-OPr) was obtained as a pale yellow crude product (yield 70%, purity (GC) 93%).

1,736 g of the crude product containing NB-Cin-OPr (MW=312.41) was purified using a molecular distillation apparatus (Short path distillatory, manufactured by UIC, model KDL 5).

Experimental conditions of the apparatus are as follows:
Pressure: 0.0021 mbar
Feed rate: 150 ml/h
Distilled part jacket temperature: 150~160° C.
Internal cooling coil temperature: 100~120° C.
Feeding part jacket temperature: 100° C.
Residue discharge temperature: 70° C.
Distillate discharge temperature: none Purification was performed as above, and as a result, 1,406 g of NB-Cin-Opr monomer was obtained in the form of white slurry (purification yield 81%, purity 99.2%)

Example 2

Purification of 2-(4-methoxy cinnamic ester)-5-norbornene 4-methoxy cinnamic acid (997.9 g, 5.6 mol), 5-norbornene-2-methanol (695 g, 5.6 mol), and zirconium (IV) acetate hydroxide (27.2 g, 0.02 eq.) were added to 100 mL of toluene, followed by agitation. Temperature was raised to 145° C. under nitrogen atmosphere to perform azeotropic reflux for 24 hours. After reaction, temperature was lowered to room temperature, and ethyl acetate was added as much as 100 v %. Extraction was performed with 1 M HCl, and washing was performed with water.

An organic layer was dried over sodium sulfate (Na$_2$SO$_4$) to remove the solvent, and as a result, 1,321 g of a highly viscous liquid compound, 2-(4-methoxy cinnamic ester)-5-norbornene (hereinafter, referred to as NB-Cin-OMe) was obtained (yield 83%, purity(GC) 94%).

1,321 g of the crude product containing NB-Cin-OMe (MW=284.35) was purified using a molecular distillation apparatus (Short path distillatory, manufactured by UIC, model KDL 5).

Experimental conditions of the apparatus are as follows:
Pressure: 0.0020~0.0026 mbar
Feed rate: 300 ml/h
Distilled part jacket temperature: 180~190° C.
Internal cooling coil temperature: 100° C.
Feeding part jacket temperature: 100° C.
Residue discharge temperature: 100° C.
Distillate discharge temperature: none Purification was performed as above, and as a result, 1,097 g of pale yellow NB-Cin-OMe monomer was obtained (purification yield 83%, purity(GC) 99.1%).

Example 3

Purification of 2-(4-F cinnamic ester)-5-norbornene

4-F cinnamic acid (1,000 g, 6 mol), 5-norbornene-2-methanol (745 g, 6 mol), and zirconium(IV) acetate hydroxide (30 g, 0.02 eq.) were added to 2 L of toluene, followed by agitation. Temperature was raised to 145° C. under nitrogen atmosphere to perform azeotropic reflux for 24 hours. After reaction, temperature was lowered to room temperature, and ethyl acetate was added as much as 100 v %. Extraction was performed with 1 M HCl, and washing was performed with water.

An organic layer was dried over sodium sulfate (Na$_2$SO$_4$) to remove the solvent, and as a result, 1,111 g of a white compound, 2-(4-F cinnamic ester)-5-norbornene (hereinafter, referred to as NB-Cin-4F) was obtained (yield 68%, purity(GC) 92%).

Two-step purification of 1,111 g of the crude product containing NB-Cin-4F (MW=272.32) was performed using a molecular distillation apparatus (Short path distillatory, manufactured by UIC, model KDL 5).

Conditions for First Preliminary Distillation (Methanol Purification)
Pressure: 5 mbar
Feeding pump speed: 0.72 L/h
Distilled part pump speed: 5~10 rpm
Residue part pump speed: 40 rpm
Body main jacket temperature: 160° C.
Condenser and distilled part temperature: 110° C.
Residue discharge temperature: 140° C.
Feeding part jacket temperature: 90° C.

As a result, it was confirmed that purification was enough to detect no methanol.

Conditions for Second Distillation
Pressure: 0.8 mbar
Feeding pump speed: 0.72 L/h
Distilled part pump speed: 10 rpm
Residue part pump speed: 40 rpm
Body main jacket temperature: 190° C.
Condenser and distilled part temperature: 140° C.
Residue discharge temperature: 140° C.
Feeding part jacket temperature: 90° C.

Purification was performed as above, and as a result, 933.3 g of white NB-Cin-4F monomer was obtained (purification yield 84%, purity(GC) 98.9%).

COMPARATIVE EXAMPLE

Comparative Example 1

Preparation of a crude product containing NB-Cin-OPr was performed in the same manner as in Example 1.

Alumina filler was dispersed in 2 L of toluene, and then slowly added to a glass tube having a diameter of 7 cm and a length of 30 cm. Continuously, toluene was slowly added thereto so that no air bubbles were remained between alumina in the glass tube. Thereafter, 100 g of the crude product containing NB-Cin-OPr was dissolved in 200 g of toluene, and the solution was slowly poured on the packed alumina. While continuously adding toluene, the NB-Cin-OPr solution purified through alumina was collected in the bottom of the glass tube. The solvent was removed from the purified NB-Cin-OPr solution to obtain a very pale yellow solid NB-Cin-OPr (purification yield 64%, purity 97.6%).

PREPARATION EXAMPLE

Preparation Example 1

Polymerization of NB-Cin-OPr

NB-Cin-OPr (5 g, 18.4 mmol) collected by the purification method of Example 1 was dissolved in 15 mL of toluene, and then agitation was performed under nitrogen blowing for 30 minutes. Temperature was raised to 90° C., and Pd(acetate)$_2$ (4.13 mg, 18.4 µmol) and tris(cyclohexyl) hydrogen phosphino tetrakis(pentafluorobenz)borate (37.2 mg, 38.6 µmol) in methylene chloride (1 mL) were added. Agitation was performed at 90° C. for 15 hours. After reaction, temperature was lowered to room temperature, and precipitates were obtained using ethanol, filtered and dried in a vacuum oven.

Yield: 91%, Mw: 203,000, PDI: 5.01

Preparation Example 2

Polymerization of NB-Cin-F

NB-Cin-F (5 g, 18.4 mmol) collected by the purification method of Example 3 was dissolved in 15 mL of toluene, and then agitation was performed under nitrogen blowing for 30 minutes. Temperature was raised to 90° C., and Pd(acetate)$_2$ (4.13 mg, 18.4 µmol) and tris(cyclohexyl) hydrogen phosphino tetrakis(pentafluorobenz)borate (37.2 mg, 38.6 µmol) in methylene chloride (1 mL) were added. Agitation was performed at 90° C. for 15 hours. After reaction, temperature was lowered to room temperature, and precipitates were obtained using ethanol, filtered and dried in a vacuum oven.

Yield: 92%, Mw: 318,000, PDI: 4.79

Comparative Preparation Example 1

Polymerization of Crude NB-Cin-OPr

Non-purified crude NB-Cin-OPr (5 g, 18.4 mmol) was dissolved in 15 mL of toluene, and then agitation was performed under nitrogen blowing for 30 minutes. Temperature was raised to 90° C., and Pd(acetate)$_2$ (4.13 mg, 18.4 µmol) and tris(cyclohexyl) hydrogen phosphino tetrakis (pentafluorobenz)borate (37.2 mg, 38.6 µmol) in methylene chloride (1 mL) were added. Agitation was performed at 90° C. for 15 hours. After reaction, temperature was lowered to room temperature, and precipitates were obtained using ethanol, filtered and dried in a vacuum oven. The yield and molecular weight of the polymer thus obtained are as follows.

Yield: 49.3%, Mw: 45,000, PDI: 2.25

Comparative Preparation Example 2

Polymerization of NB-Cin-Opr Purified by Alumina

NB-Cin-OPr (5 g, 18.4 mmol) collected by the purification method using the alumina column as in Comparative Example 1 was dissolved in 15 mL of toluene, and then agitation was performed under nitrogen blowing for 30 minutes. Temperature was raised to 90° C., and Pd(acetate)$_2$ (4.13 mg, 18.4 µmol) and tris(cyclohexyl) hydrogen phosphino tetrakis(pentafluorobenz)borate (37.2 mg, 38.6 µmol) in methylene chloride (1 mL) were added. Agitation was performed at 90° C. for 15 hours. After reaction, temperature was lowered to room temperature, and precipitates were obtained using ethanol, filtered and dried in a vacuum oven. The yield and molecular weight of the polymer thus obtained are as follows.

Yield: 87.5%, Mw: 149,000, PDI: 4.21

EXPERIMENTAL EXAMPLE

Experimental Example 1

Evaluation of Physical Properties of Monomer

APHA value, a yellowness index, of the NB-Cin-OPr monomers obtained in Example 1 and Comparative Example 1 was measured, and the result is shown in the following Table 1.

APHA value was measured as follows: 10 wt % solution was prepared by dissolving the sample in methyl chloride (MC), and then added to a cell for APHA measurement. Measurement was performed using a multifunction spectrophotometer CM-5 manufactured by Konica Minolta.

TABLE 1

| Purification method | APHA value | Note |
|---|---|---|
| Example 1 | 14 | 10 wt % MC solution |
| Crude monomer | 140 | 10 wt % MC solution |
| Comparative Example 1 | 52 | 10 wt % MC solution |

Experimental Example 2

Evaluation of Physical Properties of Polymer

Polymerization conditions and physical properties of the polymers obtained in Preparation Example 1 and Comparative Preparation Examples 1 and 2 were evaluated and the results are shown in the following Table 2.

TABLE 2

| No. | Solvent | Polymerization temperature | Polymerization time | Number average molecular weight (g/mol) | Weight average molecular weight (g/mol) | Yield |
|---|---|---|---|---|---|---|
| Preparation Example 1 | Toluene | 90° C. | 18 hr | 40,500 | 203,000 | 91% |
| Comparative Preparation Example 1 | Toluene | 90° C. | 18 hr | 20,000 | 45,000 | 49.3% |
| Comparative Preparation Example 2 | Toluene | 90° C. | 18 hr | 35,400 | 149,000 | 87.5% |

Referring to Table 2, when the compound recovered by the purification method of the present invention is used, the polymer was obtained in a yield as high as 91%, and its number average molecular weight and weight average molecular weight were higher than those of the polymer obtained by using the non-purified compound or the compound purified through the alumina column.

What is claimed is:

1. A method of purifying a photoreactive compound, the method comprising the steps of:
preparing a crude product including the photoreactive compound of the following Chemical Formula 1;
performing molecular distillation of the crude product including the photoreactive compound at a temperature of 90 to 240° C. and a pressure of 0.001 to 0.8 mbar; and
recovering the photoreactive compound:

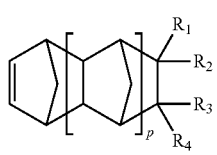

[Chemical Formula 1]

wherein p is an integer of 0 to 4,
at least one of $R_1$, $R_2$, $R_3$, and $R_4$ is a radical selected from the group consisting of Chemical Formulae 2, 3 and 4, the others are each independently hydrogen, halogen, substituted or unsubstituted $C_1$-$C_{20}$ alkyl, substituted or unsubstituted $C_2$-$C_{20}$ alkenyl, substituted or unsubstituted $C_3$-$C_{12}$ cycloalkyl, substituted or unsubstituted $C_6$-$C_{40}$ aryl, substituted or unsubstituted $C_7$-$C_{15}$ aralkyl; substituted or unsubstituted $C_2$-$C_{20}$ alkynyl, or a polar functional group including a non-hydrocarbonaceous polar group containing at least one element selected from the group consisting of oxygen, nitrogen, phosphorus, sulfur, silicon, and boron, and
if $R_1$, $R_2$, $R_3$, and $R_4$ are not hydrogen, halogen, or a polar functional group, $R_1$ and $R_2$, or $R_3$ and $R_4$ are connected to each other to form a $C_1$-$C_{10}$ alkylidene group, or $R_1$ or $R_2$ is connected to any one of $R_3$ and $R_4$ to form a $C_4$-$C_{12}$ saturated or unsaturated cyclic group or a $C_6$-$C_{24}$ aromatic ring compound;

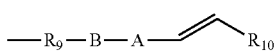

[Chemical Formula 2]

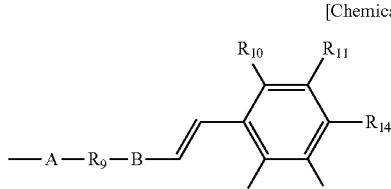

[Chemical Formula 3]

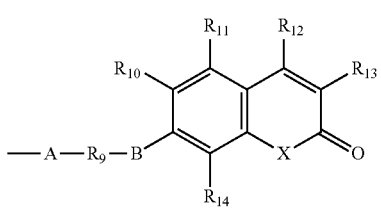

[Chemical Formula 4]

wherein A is selected from a single bond, substituted or unsubstituted $C_1$-$C_{20}$ alkylene, carbonyl, carboxyl, substituted or unsubstituted $C_6$-$C_{40}$ arylene, and substituted or unsubstituted $C_6$-$C_{40}$ heteroarylene;
B is a single bond, oxygen, sulfur, or —NH—;
X is oxygen or sulfur;
$R_9$ is selected from a single bond, substituted or unsubstituted $C_1$-$C_{20}$ alkylene, substituted or unsubstituted $C_2$-$C_{20}$ alkenylene, substituted or unsubstituted $C_3$-$C_{12}$ cycloalkylene, substituted or unsubstituted $C_6$-$C_{40}$ arylene, substituted or unsubstituted $C_7$-$C_{15}$ aralkylene, and substituted or unsubstituted $C_2$-$C_{20}$ alkynylene; and
$R_{10}$, $R_{11}$, $R_{12}$, $R_{13}$, and $R_{14}$ are the same as or different from each other, and each independently selected from the group consisting of hydrogen, a hydroxy group, a halogen group, substituted or unsubstituted $C_7$-$C_{15}$ aralkyl, substituted or unsubstituted $C_2$-$C_{20}$ alkynyl, substituted or unsubstituted $C_1$-$C_{20}$ alkyl, substituted or unsubstituted $C_1$-$C_{20}$ alkoxy, substituted or unsubstituted $C_6$-$C_{30}$ aryloxy, substituted or unsubstituted $C_6$-$C_{40}$ aryl, $C_6$-$C_{40}$ heteroaryl including a heteroatom of Group 14, Group 15, or Group 16, and substituted or unsubstituted $C_6$-$C_{40}$ alkoxyaryl.

2. The method of claim 1, wherein $R_1$ of Chemical Formula 1 is a compound of Chemical Formula 2, and at least one of $R_2$, $R_3$, and $R_4$ is selected from the group consisting of Chemical Formulae 2, 3 and 4.

3. The method of claim 1, wherein the non-hydrocarbonaceous polar group includes the following compounds:
one or more selected from the group consisting of —$OR_6$, —$R_5OR_6$, —OC(O)$OR_6$, —$R_5OC(O)OR_6$, —C(O)$OR_6$, —$R_5C(O)OR_6$, —C(O)$R_6$, —$R_5C(O)R_6$, —OC(O)$R_6$, —$R_5OC(O)R_6$, —($R_5O)_p$—$OR_6$(p is an integer of 1 to 10), —($OR_5)_p$—$OR_6$(p is an integer of 1 to 10), —C(O)—O—C(O)$R_6$, —$R_5C(O)$—O—C(O)$R_6$, —$SR_6$, —$R_5SR_6$, —$SSR_6$, —$R_5SSR_6$, —S(═O)$R_6$, —$R_5S$(═O)$R_6$, —$R_5C$(═S)$R_6$, —$R_5C$(═S)$SR_6$, —$R_5SO_3R_6$, —$SO_3R_6$, —$R_5N$═C═S, —N═C═S, —NCO, $R_5$—NCO, —CN, —$R_5CN$, —NNC(═S)$R_6$, —$R_5NNC$(═S)$R_6$, —$NO_2$, —$R_5NO_2$,

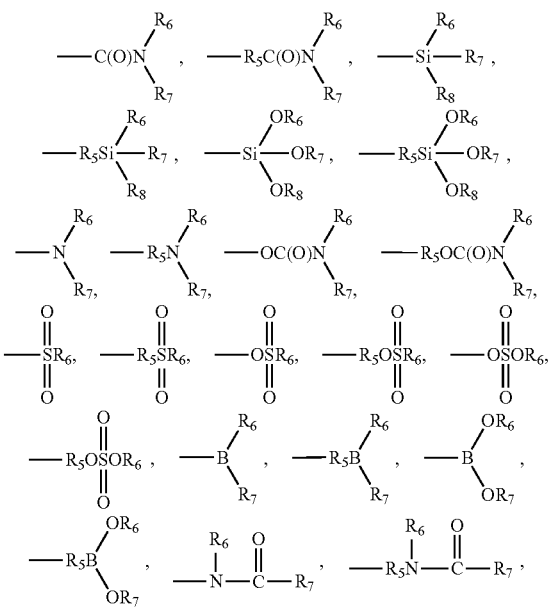

-continued

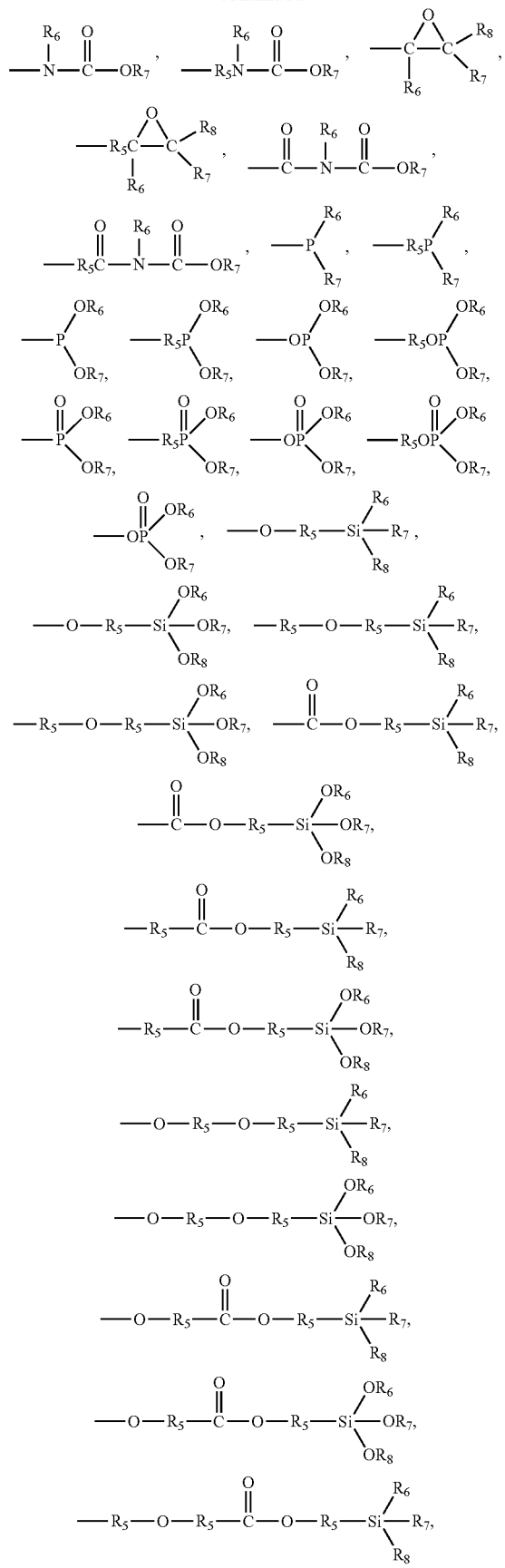

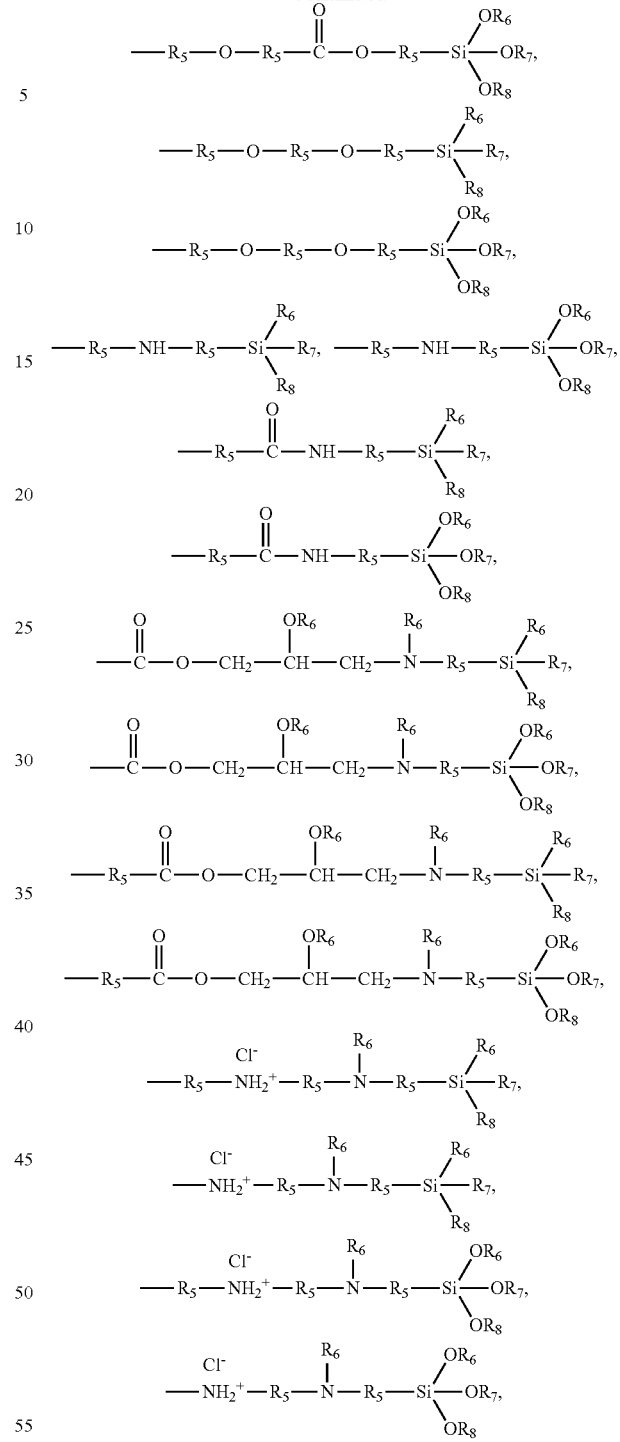

in the functional groups, each $R_5$ is selected from substituted or unsubstituted $C_1$-$C_{20}$ alkylene, substituted or unsubstituted $C_2$-$C_{20}$ alkenylene, substituted or unsubstituted $C_3$-$C_{12}$ cycloalkylene, substituted or unsubstituted $C_6$-$C_{40}$ arylene, substituted or unsubstituted $C_7$-$C_{15}$ aralkylene, and substituted or unsubstituted $C_2$-$C_{20}$ alkynylene, and $R_6$, $R_7$, and $R_8$ are each independently selected from hydrogen, halogen, substituted or unsubstituted $C_1$-$C_{20}$ alkyl, substituted or unsubstituted $C_2$-$C_{20}$ alkenyl, substituted or unsubstituted $C_3$-$C_{12}$ cycloalkyl, substituted or unsubstituted $C_6$-$C_{40}$ aryl, substituted or unsubstituted $C_7$-$C_{15}$ aralkyl, and substituted or unsubstituted $C_2$-$C_{20}$ alkynyl.

4. The method of claim 1, wherein $C_6$-$C_{40}$ aryl and $C_6$-$C_{40}$ heteroaryl containing a heteroatom of Group 14, 15, or 16 in the substituents includes the following Chemical Formulae:

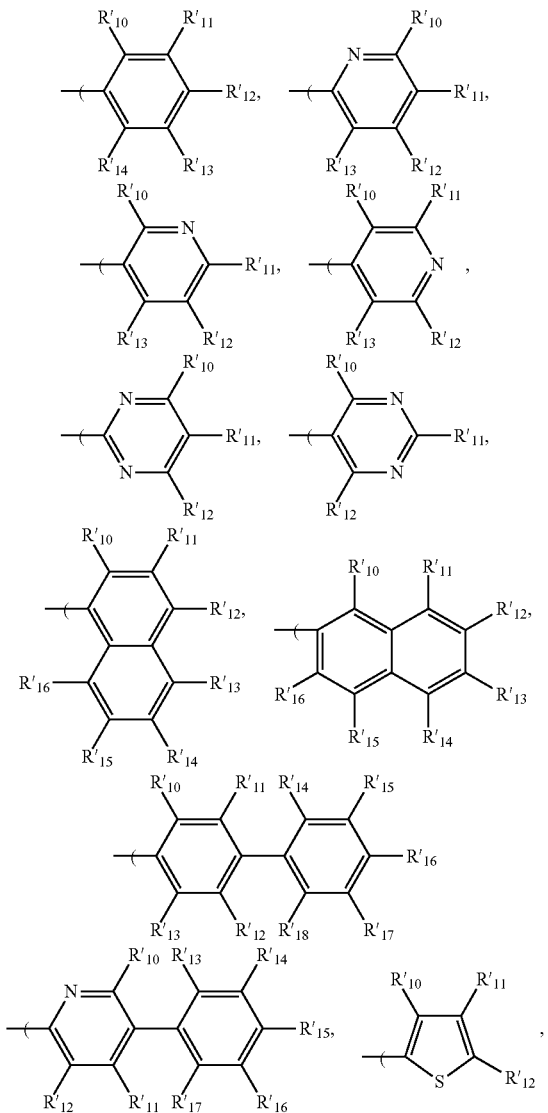

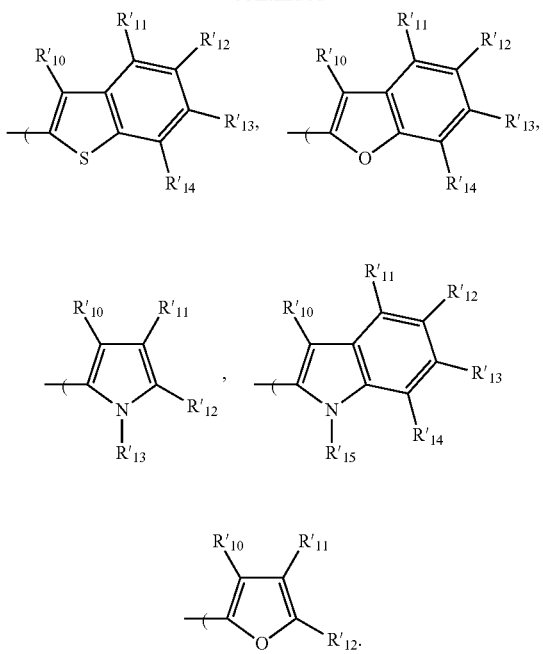

wherein at least one of $R'_{10}$ to $R'_{18}$ should be substituted or unsubstituted $C_1$-$C_{20}$ alkoxy, or substituted or unsubstituted $C_6$-$C_{30}$ aryloxy, and the others are each independently selected from the group consisting of substituted or unsubstituted $C_1$-$C_{20}$ alkyl, substituted or unsubstituted $C_1$-$C_{20}$ alkoxy, substituted or unsubstituted $C_6$-$C_{30}$ aryloxy, and substituted or unsubstituted $C_6$-$C_{40}$ aryl.

5. The method of claim 1, wherein the photoreactive compound has a boiling point of 180° C. or higher.

6. The method of claim 1, further comprising a step of performing preliminary distillation at a temperature of 20 to 200° C. and a pressure of 0.01 to 100 mbar, prior to the step of performing molecular distillation of the crude product.

7. The method of claim 1, wherein the photoreactive compound recovered after molecular distillation has purity of 90% or higher.

8. The method of claim 1, wherein the photoreactive compound recovered after molecular distillation has an APHA value of less than 50.

* * * * *